US010939979B2

(12) United States Patent
Lombardi

(10) Patent No.: US 10,939,979 B2
(45) Date of Patent: Mar. 9, 2021

(54) DENTAL BITE BLOCK DEVICE

(71) Applicant: Domenic G. Lombardi, Brookfield, OH (US)

(72) Inventor: Domenic G. Lombardi, Brookfield, OH (US)

( * ) Notice: Subject to any disclaimer, the term of this patent is extended or adjusted under 35 U.S.C. 154(b) by 240 days.

(21) Appl. No.: 16/204,490

(22) Filed: Nov. 29, 2018

(65) Prior Publication Data

US 2020/0170754 A1 Jun. 4, 2020

(51) Int. Cl.
*A61C 5/00* (2017.01)
*A61C 9/00* (2006.01)
*A61C 17/06* (2006.01)
*A61K 6/90* (2020.01)

(52) U.S. Cl.
CPC ............. *A61C 5/007* (2013.01); *A61C 9/0006* (2013.01); *A61C 17/04* (2013.01); *A61K 6/90* (2020.01); *A61C 2201/007* (2013.01)

(58) Field of Classification Search
CPC ......... A61C 5/007; A61C 5/90; A61C 9/0006; A61C 9/00; A61C 17/04; A61C 17/06; A61C 2201/007; A61K 6/90
USPC .......................................................... 433/93
See application file for complete search history.

(56) References Cited

U.S. PATENT DOCUMENTS

| | | | | | |
|---|---|---|---|---|---|
| 2,220,674 | A | * | 11/1940 | Bloomheart | A61C 5/90 600/238 |
| 2,823,455 | A | * | 2/1958 | Sprague | A61C 17/08 433/93 |
| 3,483,619 | A | * | 12/1969 | Smith | A61B 1/24 433/140 |
| 4,167,814 | A | * | 9/1979 | Schubert | A61C 17/08 433/93 |
| 4,802,851 | A | * | 2/1989 | Rhoades | A61C 17/08 433/93 |
| 4,975,057 | A | * | 12/1990 | Dyfvermark | A61C 17/08 433/93 |
| 5,588,836 | A | * | 12/1996 | Landis | A61C 17/08 433/93 |
| 6,652,276 | B2 | | 11/2003 | Fischer et al. | |
| 8,292,620 | B2 | * | 10/2012 | Black | A61C 17/08 433/93 |

(Continued)

OTHER PUBLICATIONS

Nagori et al., Custom-made mouth prop for TMJ arthrocentesis: a technical note, Oral Maxillofacial Surgery, Mar. 2017, vol. 21, Issue 1, pp. 75-77, Springer-Verlag Berlin Heidelberg, first published online Nov. 29, 2016.

*Primary Examiner* — Matthew M Nelson

(57) ABSTRACT

A dental bite block device includes a front wall, a flat lateral sidewall, and a concave lateral sidewall that define a longitudinal channel that extends through the device. The lateral sidewalls are connected by a crossbar, and the channel can be filled with polyvinyl siloxane (PVS) dental impression putty. When the device is positioned in the patient's mouth, the flat lateral sidewall faces the right inner check of the patient, the patient's tongue rests against the concave lateral sidewall, and the patient's upper and lower teeth rest open on the front wall. Once the PVS putty sets, it forms a solid half cylinder-shaped member that includes impressions of a plurality of the patient's upper and lower teeth, which assist to maintain the device in place. The front wall and concave sidewall further include an opening that defines a clip for a saliva ejector.

20 Claims, 3 Drawing Sheets

(56) References Cited

U.S. PATENT DOCUMENTS

| | | | | |
|---|---|---|---|---|
| 8,870,568 | B1* | 10/2014 | Ream | A61C 17/08 433/93 |
| 9,089,389 | B2* | 7/2015 | Hirsch | A61C 1/088 |
| 9,968,341 | B2* | 5/2018 | Ritter | A61B 1/24 |
| 10,561,310 | B2* | 2/2020 | Lutz | A61B 90/30 |
| 2004/0033468 | A1* | 2/2004 | Fischer | A61C 5/90 433/140 |
| 2005/0239018 | A1* | 10/2005 | Green | A61C 5/90 433/140 |
| 2008/0318183 | A1* | 12/2008 | Suzman | A61C 5/90 433/93 |
| 2011/0229847 | A1* | 9/2011 | Worthington | A61C 17/08 433/93 |
| 2014/0356802 | A1* | 12/2014 | Balog | A61B 1/24 433/29 |
| 2015/0335394 | A1* | 11/2015 | Khouri | A61C 5/90 433/29 |
| 2019/0357992 | A1* | 11/2019 | Calhoun | A61B 13/00 |

* cited by examiner

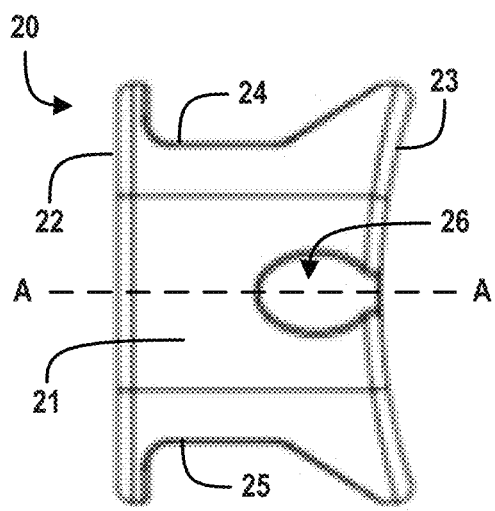
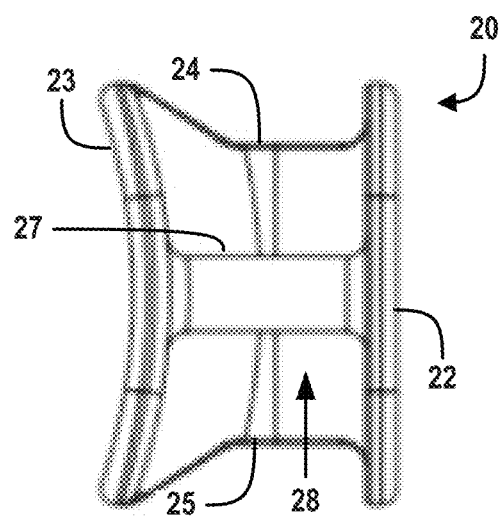
FIG. 2A  FIG. 2B
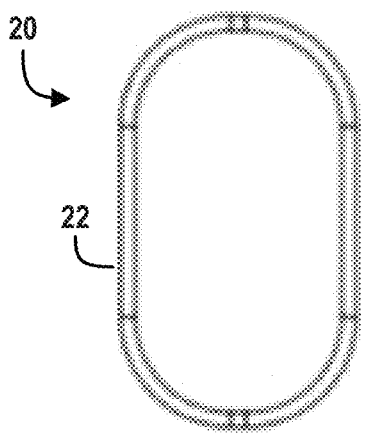
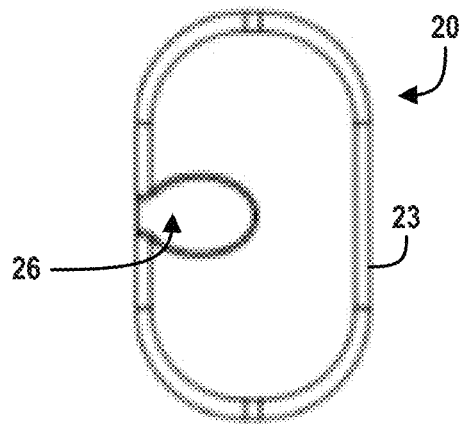
FIG. 3A  FIG. 3B
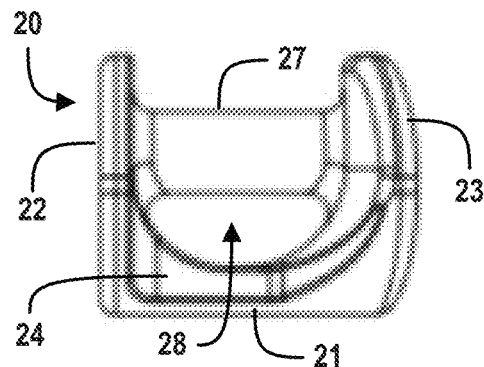
FIG. 4

DENTAL BITE BLOCK DEVICE

FIELD

The present invention relates generally to dental devices. More specifically, the invention relates to dental bite block devices used to prop the mouth of a patient open during a dental procedure.

BACKGROUND

A dentist may employ a mouth prop or bite block to maintain the mouth of a patient in an open position when performing a dental procedure. Some dental bite blocks can be customized to include an impression of the patient's teeth, which helps to keep the bite block in place during use and results in a better fit and greater comfort for the patient.

FIGS. 1A and 1B illustrate a prior art customizable dental bite block according to U.S. Pat. No. 6,652,276. As shown, the bite block 10 has a rigid body 11 that fits between the upper teeth 12 and lower teeth 13 of a patient's mouth while in an open position. The rigid body 11 is angled to provide upper and lower surfaces 14, 15 that contact and engage the patient's upper and lower teeth 12, 13. The bite block 10 further includes an outer shoulder 16 and an inner shoulder 17 that extend from the sides of the rigid body 11 to define upper and lower channels 18, 19 into which the patient's upper and lower teeth 12, 13 can be inserted. The upper and lower surfaces 14, 15 of the rigid body 11 are constructed of a plastically deformable impression material so that when the bite block 10 is inserted into the patient's mouth, the upper and lower surfaces 14, 15 can form and retain impressions of the patient's upper and lower teeth 12, 13.

Constructing the upper and lower surfaces 14, 15 of the rigid body 11 from a plastically deformable material allows the bite block 10 to provide a customized and comfortable fit. The dental impressions formed in the upper and lower surfaces 14, 15 of the rigid body 11 engage the patient's teeth and reduce the likelihood that the bite block 10 will slip from between the patient's teeth when holding the patient's mouth open. However, the bite block 10 still employs a wedge force to maintain its position during use and may not achieve the level of stability required or desired by the dentist. Furthermore, constructing the bite block 10 of both rigid and deformable materials increases the complexity of the manufacture. Accordingly, there is a need for a dental bite block device that provides customization, increased stability and an improved design.

SUMMARY

A dental bite block device includes a front wall, a flat lateral sidewall, and a concave lateral sidewall that define a substantially U-shaped longitudinal channel that extends through the device. The lateral sidewalls are connected by a crossbar, and the channel can be filled with polyvinyl siloxane (PVS) dental impression putty. When the dental bite block device is positioned in the patient's mouth, the flat lateral sidewall faces the right inner check of the patient, the patient's tongue rests against the concave lateral sidewall, and the patient's upper and lower teeth rest open on the front wall. Once the PVS putty cures and sets, it forms a solid half cylinder-shaped member that includes dentition impressions of a plurality of the patient's upper and lower teeth, which assist to maintain the dental bite block device in place during use. The front wall and concave sidewall further include an opening that defines a clip for a saliva ejector where the tip of the saliva ejector rests next to the patient's tongue when the device is in use.

The foregoing summary is explanatory only and not restrictive of various aspects as claimed. It is provided to introduce a selection of concepts in a simplified form that are further described below in the detailed description. Other features and embodiments of the present invention will be apparent to one with skill in the art upon review of the following detailed description and the appended drawings. It is intended that all such additional features and embodiments are to be within the scope of the present invention and protected by the accompanying claims.

BRIEF DESCRIPTION OF THE DRAWINGS

FIGS. 2A and 2B illustrate front and rear views of a dental bite block device in accordance with aspects of the present invention.

FIGS. 3A and 3B illustrate side views of a dental bite block device in accordance with aspects of the present invention.

FIG. 4 illustrates a top view of a dental bite block device in accordance with aspects of the present invention.

DETAILED DESCRIPTION

Figure 1A:
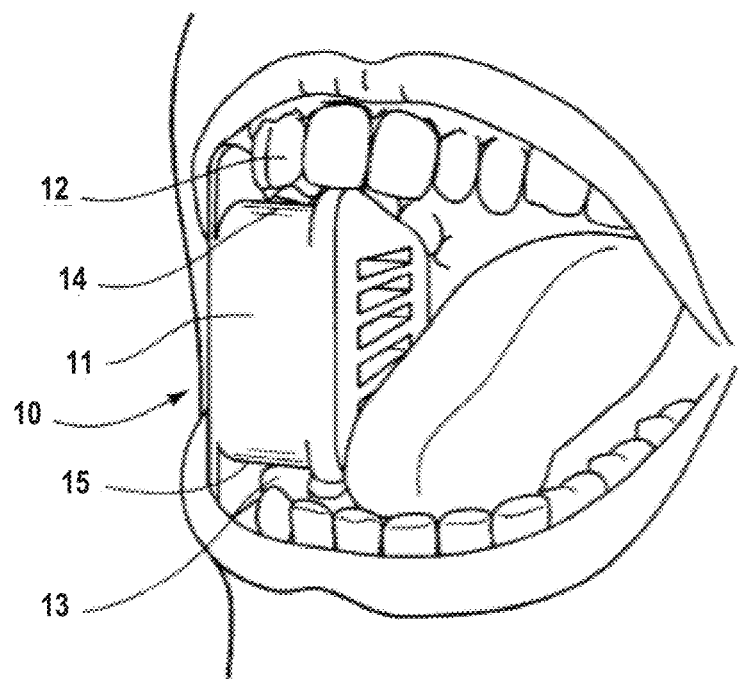
FIGS. 1A and 1B illustrate a prior art customizable dental bite block.
Figure 1B:
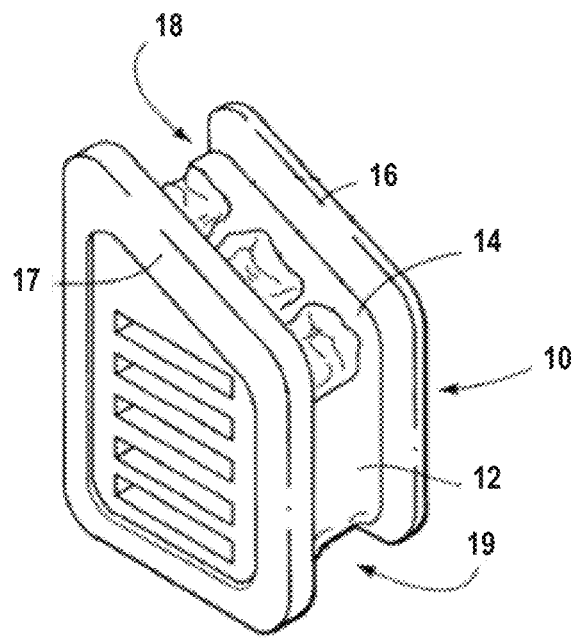

Various aspects of the present invention are described below with reference to the drawings, wherein like numerals generally refer to like or corresponding elements throughout. The drawings and detailed description are not intended to limit the claimed subject matter to the specific embodiment described. Rather, the intention is to cover all modifications, equivalents and alternatives falling within the spirit and scope of the claimed subject matter.

FIG. 2A illustrates a front view of a dental bite block device 20 in accordance with aspects of the present invention. In general, dental bite block device 20 is structured and arranged to maintain the mouth of a patient in an open position during a dental procedure. In one embodiment, the dental bite block device 20 is constructed of a single type of rigid plastic material and is molded as a unitary piece.

As shown, the dental bite block device 20 includes a front wall 21 and lateral sidewalls 22, 23. In use, front wall 21 is positioned toward the front of the patent's mouth, the upper and lower teeth of the patient rest open on front wall 21, lateral sidewall 22 faces the inner cheek of the patient, and the tongue of the patient rests against lateral sidewall 23. The lateral sidewall 22 has a generally flat surface, and lateral sidewall 23 has a concave surface defining a concavity where the patient's tongue rests during use. In one embodiment, the distance between flat lateral sidewall 22 and concave lateral sidewall 23 is approximately 0.98 inches.

The height of the front wall 21 is based on the average mouth opening dimension of adult and pediatric patients. If the patient has a larger mouth opening, then dental bite block device 20 is placed further toward the back teeth. If the patient has a smaller mouth opening, then dental bite block device 20 is placed further toward the front teeth. In one embodiment, the height of the front wall is approximately 1.0 inch.

When dental bite block device 20 is used in the depicted orientation, lateral sidewall 22 is positioned to face the right inner check of the patient, the patient's upper teeth rest open on surface 24 of front wall 21, and the patient's lower teeth rest open on surface 25 of front wall 21. It can be appreciated that dental bite block device 20 is symmetrical about horizontal line AA and can be rotated such that lateral sidewall 22 is positioned to face the inner left check of the patient, the patient's upper teeth rest open on contact surface 25 of front wall 21, and the patient's lower teeth rest open on contact surface 24 of front wall 21. As shown, front wall 21 further includes an opening 26, which defines a clip for a saliva ejector (not shown) where the tip of the saliva ejector rests next to the patient's tongue when the device is in use.

FIG. 2B illustrates a rear view of dental bite block device 20. As shown, flat lateral sidewall 22 and concave lateral sidewall 23 are parallel to each other and connected to each other by a crossbar 27. The front wall 21 and the lateral sidewalls 22, 23 are configured to define a substantially U-shaped longitudinal channel 28 that extends through dental bite block device 20 and passes under crossbar 27. The channel 28 is structured and arranged to receive and contain a volume of polyvinyl siloxane (PVS) dental impression putty. The PVS putty is a viscous liquid that can be inserted into and fill channel 28 for forming upper and lower dental impressions that assist in maintaining dental bite block device 20 in place during use. The dental bite block device 20 can be provided as part of a kit that includes a tube, jar or other separate container of PVS putty. In one embodiment, the channel 28 is configured to receive approximately 0.45 cubic inches (~7.37 cc) of PVS putty, and the kit includes a tube containing between 0.5 cubic inches and 1.0 cubic inch of PVS putty. The kit can further include a syringe, spatula or other device for inserting the PVS putty into channel 28.

After channel 28 is filled with the PVS putty, the dental bite block device 20 is positioned in the patient's mouth such that the upper and lower teeth of the patient rest open on wall front wall 21 as the PVS putty is setting. In the depicted orientation, the patient's upper teeth rest on contact surface 24 of front wall 21, and the patient's lower teeth rest on contact surface 25 of front wall 21. The PVS putty is placed under and is secured by crossbar 27, which adds stability to the PVS putty once it sets. When the PVS putty cures and sets, it forms a solid half cylinder-shaped member within channel 28 that includes dentition impressions of a plurality of the patient's upper and lower teeth on its top and bottom surfaces. For instance, depending on the size of the patient's mouth opening, the PVS putty can engage and form an impression as far anterior as the distal of the lateral incisors and posteriorly as far as the distal of the third molars, for both the patient's maxillary and mandibular teeth.

FIG. 3A illustrates a side view of dental bite block device 20. As shown, flat lateral sidewall 22 has a generally oval or geometric stadium shape. In use, the outer surface of flat lateral sidewall 22 is positioned against the inner cheek of the patient, and the inner surface of lateral sidewall contacts and functions to contains the PVS putty. In one embodiment, flat lateral sidewall 22 is approximately 1.4 inches high and approximately 0.8 inches wide.

FIG. 3B illustrates a side view of dental bite block device 20. As shown, concave lateral sidewall 23 has a generally oval or geometric stadium shape. In use, the patient's tongue rests against the concavity in the outer surface of lateral sidewall 23, and the inner surface of lateral sidewall 23 contacts and functions to contain the PVS putty. The concave lateral sidewall 23 further includes opening 26, which defines a clip for a saliva ejector (not shown) where the tip of the saliva ejector rests next to the patient's tongue when the device is in use. In one embodiment, concave lateral sidewall 23 is approximately 1.4 inches high and approximately 0.8 inches wide.

FIG. 4 illustrates a top view of dental bite block device 20. As shown, front wall 21, flat lateral sidewall 22 and concave lateral sidewall 23 define U-shaped longitudinal channel 28 that extends through dental bite block device 20 and passes under crossbar 27. The PVS putty is placed under and is secured by crossbar 27, which adds stability to the PVS putty once it sets. After channel 28 is filled with the PVS putty, the dental bite block device 20 is positioned in the patient's mouth, and the upper teeth of the patient rest open on contact surface 24 of front wall 21. When the PVS putty cures and sets, it forms a solid half cylinder-shaped member within channel 28 that includes dentition impressions of a plurality of the patient's upper and lower teeth on its top and bottom surfaces.

Figure 5A:
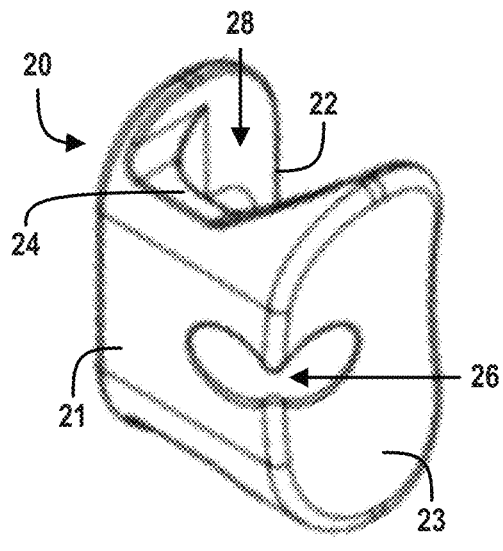
FIGS. 5A and 5B illustrate perspective views of a dental bite block device in accordance with aspects of the present invention.

FIG. 5A illustrates a perspective view of dental bite block 20. As shown, front wall 21 and concave lateral sidewall 23 include opening 26, which defines a clip for a saliva ejector (not shown) where the tip of the saliva ejector rests next to the patient's tongue when the device is in use. The inner surfaces of front wall 21, flat lateral sidewall 22 and concave lateral sidewall 23 define substantially U-shaped longitudinal channel 28 that extends through dental bite block device 20. After channel 28 is filled with the PVS putty, the dental bite block device 20 is positioned in the patient's mouth, and the upper teeth of the patient rest open on contact surface 24 of front wall 21. Once the PVS putty cures and sets in channel 28, the dental bite block device 20 is secure and stable and the saliva ejector can be placed in the clip defined by opening 26.

Figure 5B:
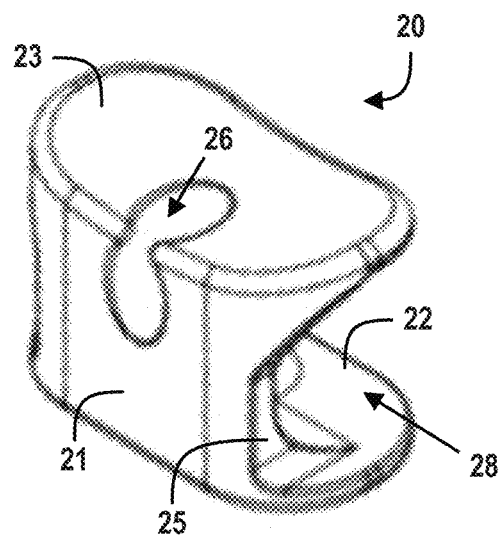

FIG. 5B illustrates a perspective view of dental bite block device 20. As shown, front wall 21 and concave lateral sidewall 23 include opening 26, which defines a clip for a saliva ejector (not shown) where the tip of the saliva ejector rests next to the patient's tongue when the device is in use. The inner surfaces of front wall 21, flat lateral sidewall 22 and concave lateral sidewall 23 define substantially U-shaped longitudinal channel 28 that extends through dental bite block device 20. After channel 28 is filled with the PVS putty, the dental bite block device 20 is positioned in the patient's mouth, and the lower teeth of the patient rest open on contact surface 25 of front wall 21. Once the PVS putty cures and sets in channel 28, the dental bite block device 20 is secure and stable and the saliva ejector can be placed in the clip defined by opening 26.

Figure 6A:
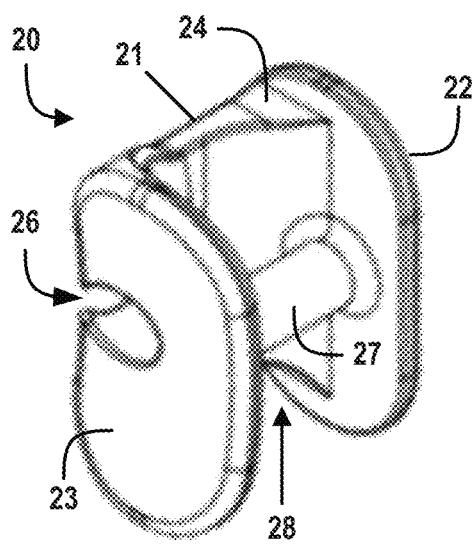
FIGS. 6A and 6B illustrate perspective views of a dental bite block device in accordance with aspects of the present invention.

FIG. 6A illustrates a perspective view of dental bite block device 20. As shown, flat lateral sidewall 22 and concave lateral sidewall 23 are parallel to each other and connected to each other by crossbar 27. The inner surfaces of front wall 21 and the lateral sidewalls 22, 23 define a substantially U-shaped longitudinal channel 28 that extends through dental bite block device 20 and passes under crossbar 27. After longitudinal channel 28 is filled with PVS putty, the dental bite block device 20 is positioned in the patient's mouth. In the depicted orientation, flat lateral sidewall 22 is positioned to face the right inner check of the patient, the patient's tongue rests against concave lateral sidewall 23, and the patient's upper teeth rest open on contact surface 24 of front wall 21. The PVS putty is placed under and is secured by crossbar 27, which adds stability to the PVS putty once it sets. When the PVS putty cures and sets, it forms a solid half cylinder-shaped member within channel 28 that includes dentition impressions of a plurality of the patient's upper and lower teeth on its top and bottom surfaces, which assist in maintaining dental bite block device 20 in place during use. After the PVS putty sets in channel 28 and the dental bite block device 20 is secure and stable, the saliva ejector can be placed in the clip defined by opening 26.

Figure 6B:
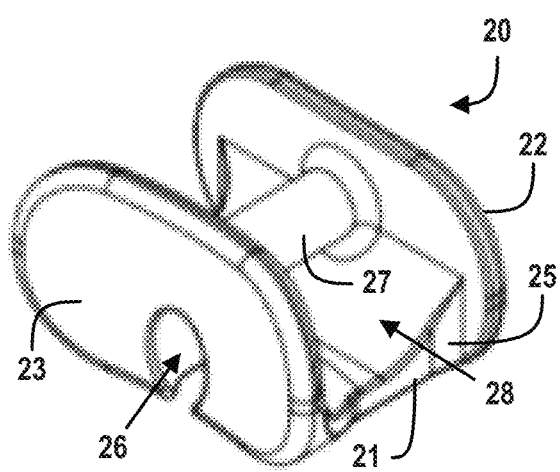

FIG. 6B. illustrates a perspective view of dental bite block device 20. As shown, flat lateral sidewall 22 and concave lateral sidewall 23 are parallel to each other and connected to each other by crossbar 27. The inner surfaces of front wall 21 and the lateral sidewalls 22, 23 define a substantially U-shaped longitudinal channel 28 that extends through dental bite block device 20 and passes under crossbar 27. After longitudinal channel 28 is filled with PVS putty, the dental bite block device 20 is positioned in the patient's mouth. In the depicted orientation, flat lateral sidewall 22 is positioned to face the right inner check of the patient, the patient's tongue rests against concave lateral sidewall 23, and the patient's lower teeth rest open on contact surface 25 of front wall 21. The PVS putty is placed under and is secured by crossbar 27, which adds stability to the PVS putty once it sets. When the PVS putty cures and sets, it forms a solid half cylinder-shaped member within channel 28 that includes dentition impressions of a plurality of the patient's upper and lower teeth on its top and bottom surfaces, which assist in maintaining dental bite block device 20 in place during use. After the PVS putty sets in channel 28 and the dental bite block device 20 is secure and stable, the saliva ejector can be placed in the clip defined by opening 26.

The detailed description and appended drawings support various aspects of an improved dental bite block device. By way of illustration and not limitation, supported aspects include a dental bite block device having a front wall, a flat lateral sidewall, and a concave lateral sidewall that define a substantially U-shaped longitudinal channel that extends through the device. The flat and concave lateral sidewalls are connected by a crossbar, and the longitudinal channel can be filled with PVS dental impression putty. When the dental bite block device is positioned in the patient's mouth, the flat lateral sidewall faces the right inner check of the patient, the patient's tongue rests against the concave lateral sidewall, and the patient's upper and lower teeth rest open on the front wall. If the patient has a larger mouth opening, then dental bite block device is placed further toward the back teeth. If the patient has a smaller mouth opening, then dental bite block device is placed further toward the front teeth. Once the PVS putty cures and sets, it forms a solid half cylinder-shaped member that includes dentition impressions of a plurality of the patient's upper and lower teeth, which assist to maintain the device in place. The front wall and concave sidewall further include an opening that defines a clip for a saliva ejector. The dental bite block device can be provided as part of a kit that includes a separate container of PVS putty. The kit can further include a syringe, spatula or other dispensing device for inserting the PVS putty into the channel. These supported aspects and others described above provide various attendant and/or technical advantages including customization, increased stability and an improved design.

The detailed description above and the accompanying drawings are exemplary and not intended to represent the only form in which the present invention can be constructed or used. While certain shapes and dimensions may be described in connection with an embodiment, the scope of the present invention is intended to encompass other shapes and dimensions that are consistent with aspects of the present invention. Those of ordinary skill in the art will recognize additional modifications and variations of the present invention. The following claims are intended to cover all such modifications and variations of the described embodiments.

What is claimed is:

1. A dental bite block device for maintaining a patient's mouth in an open position, the dental bite block device comprising:
    a front wall having a maxillary teeth contact surface and a mandibular teeth contact surface; and
    lateral sidewalls connected by a crossbar, the front wall and lateral sidewalls defining a substantially U-shaped longitudinal channel that passes under the crossbar and extends through the dental bite block device from the maxillary teeth contact surface of the front wall to the mandibular teeth contact surface of the front wall,
    wherein the dental bite block device is structured and arranged to receive and contain a volume of dental impression putty within the channel and under the crossbar, and the crossbar is structured and arranged to secure the dental impression putty within the channel.

2. The dental bite block device of claim 1, wherein the crossbar connecting the lateral sidewalls is cylindrical.

3. The dental bite block device of claim 1, wherein the lateral sidewalls comprise:
    a lateral sidewall having a flat surface; and
    a lateral sidewall having a concave surface defining a concavity where the patient's tongue rests.

4. The dental bite block device of claim 3, wherein the lateral sidewall having the concave surface and the front wall include an opening that defines a clip for a saliva ejector.

5. The dental bite block device of claim 3, wherein the lateral sidewalls are stadium-shaped.

6. The dental bite block device of claim 1, wherein the front wall is approximately 1.0 inch high.

7. The dental bite block device of claim 1, wherein the volume of dental impression putty is approximately 0.45 cubic inches.

8. The dental bite block device of claim 1, wherein the dental impression putty is polyvinyl siloxane dental impression putty.

9. A dental bite block kit for maintaining a patient's mouth in an open position, the kit comprising:
    a dental bite block device having a front wall and lateral sidewalls, the front wall having a maxillary teeth contact surface and a mandibular teeth contact surface, the lateral sidewalls connected by a crossbar, the front wall and lateral sidewalls defining a substantially U-shaped longitudinal channel that passes under the crossbar and extends through the dental bite block device from the maxillary teeth contact surface of the front wall to the mandibular teeth contact surface of the front wall, wherein the dental bite block device is structured and arranged to receive and contain a volume of dental impression putty within the channel and under the crossbar, and the crossbar is structured and arranged to secure the dental impression putty within the channel; and
    a separate container of the dental impression putty.

10. The dental bite block kit of claim 9, wherein the crossbar connecting the lateral sidewalls is cylindrical.

11. The dental bite block kit of claim 9, wherein the volume of dental impression putty is approximately 0.45 cubic inches.

12. The dental bite block kit of claim 11, wherein the dental impression putty is polyvinyl siloxane dental impression putty.

13. The dental bite block kit of claim 11, wherein the separate container contains between 0.5 cubic inches and 1.0 cubic inch of dental impression putty.

14. The dental bite block kit of claim 13, wherein the dental impression putty is polyvinyl siloxane dental impression putty.

15. The dental bite block kit of claim 11, further comprising a dispensing device for inserting the dental impression putty into the channel.

16. A dental method for maintaining a patient's mouth in an open position during a dental procedure, the method comprising:
    inserting a volume of dental impression putty into a dental bite block device having a front wall and lateral sidewalls, the front wall having a maxillary teeth contact surface and a mandibular teeth contact surface, the lateral sidewalls connected by a crossbar, the front wall and lateral sidewalls defining a substantially U-shaped longitudinal channel that passes under the crossbar and extends through the dental bite block device from the maxillary teeth contact surface of the front wall to the mandibular teeth contact surface of the front wall, wherein the dental impression putty is inserted into the channel and under the crossbar, and the crossbar secures the dental impression putty within the channel;
    positioning the dental bite block device in the patient's mouth; and
    allowing the dental impression putty to cure and form impressions of a plurality of the patient's upper and lower teeth.

17. The dental method of claim 16, wherein the plurality of the patient's upper and lower teeth includes the lateral incisors and third molars.

18. The dental method of claim 16, further comprising:
    attaching a saliva ejector device to a clip defined by an opening in the front wall and one of the lateral sidewalls.

19. The dental method of claim 16, wherein the volume of dental impression putty is approximately 0.45 cubic inches.

20. The dental method of claim 19, wherein the dental impression putty is polyvinyl siloxane dental impression putty.

* * * * *